(12) United States Patent  
Schmidt-Forst et al.

(10) Patent No.: US 8,912,383 B2  
(45) Date of Patent: *Dec. 16, 2014

(54) DUAL MODE ABSORBENT TAMPON

(71) Applicant: Kimberly-Clark Worldwide, Inc., Neenah, WI (US)

(72) Inventors: Alexander Schmidt-Forst, Appleton, WI (US); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/621,359

(22) Filed: Sep. 17, 2012

(65) Prior Publication Data

US 2013/0018342 A1    Jan. 17, 2013

Related U.S. Application Data

(63) Continuation of application No. 11/117,899, filed on Apr. 29, 2005, now Pat. No. 8,293,968.

(51) Int. Cl.
*A61F 13/15* (2006.01)
*A61F 13/20* (2006.01)

(52) U.S. Cl.
CPC ......... *A61F 13/2085* (2013.01); *A61F 13/2051* (2013.01)
USPC ................. 604/365; 604/11; 604/12; 604/13; 604/14; 604/15; 604/358; 604/363

(58) Field of Classification Search
USPC .............................. 604/365, 11–15, 358, 363
See application file for complete search history.

(56) References Cited

U.S. PATENT DOCUMENTS

| | | | | |
|---|---|---|---|---|
| 1,887,526 A | * | 11/1932 | Spielberg et al. | 604/287 |
| 2,123,750 A | * | 7/1938 | Schulz | 604/365 |
| 2,386,590 A | | 10/1945 | Vernon | |
| 2,499,414 A | * | 3/1950 | Rabell | 604/377 |

(Continued)

FOREIGN PATENT DOCUMENTS

| | | |
|---|---|---|
| EP | 0 108 637 A2 | 5/1984 |
| EP | 0 149 155 A2 | 7/1985 |

(Continued)

OTHER PUBLICATIONS

Gauze, definition, Internet web page "http://dictionary.reference.com/browse/gauze", viewed and printed Feb. 14, 2014, 2 pages.

*Primary Examiner* — Michele M Kidwell
(74) *Attorney, Agent, or Firm* — Kimberly-Clark Worldwide, Inc.

(57) ABSTRACT

A dual mode absorbent tampon comprising a mass of absorbent material compressed into a generally cylindrical shape, in a first mode of the tampon. The mass of absorbent material comprising a homogeneous mixture of a plurality of fibers which comprise at least a first type of fiber and a second type of fiber, where the first type of fiber is bondable to fibers of the plurality of fibers. At least a portion of the first type of fibers are bonded in a pre-determined pattern to adjacent fibers of the plurality of fibers wherein absorption by the tampon causes at least a portion of the mass of absorbent material to expand into a non-cylindrical shape which is dependent upon the pre-determined pattern, in a second mode of the tampon.

16 Claims, 1 Drawing Sheet

(56) References Cited

U.S. PATENT DOCUMENTS

| | | | |
|---|---|---|---|
| 2,926,394 A * | 3/1960 | Bletzinger et al. ............ 28/120 |
| 3,068,867 A * | 12/1962 | Bletzinger et al. ............ 604/15 |
| 3,572,341 A | 3/1971 | Glassman |
| 3,628,534 A | 12/1971 | Donohue |
| 3,670,731 A | 6/1972 | Harmon |
| 3,710,793 A | 1/1973 | Glassman |
| 3,731,687 A | 5/1973 | Glassman |
| 3,732,866 A | 5/1973 | Accavallo |
| 3,738,364 A * | 6/1973 | Brien et al. ................. 604/375 |
| 3,854,481 A | 12/1974 | Messing |
| 3,946,737 A * | 3/1976 | Kobler ................. 604/385.18 |
| 4,109,354 A | 8/1978 | Ronc |
| 4,200,101 A | 4/1980 | Glassman |
| 4,217,900 A | 8/1980 | Wiegner et al. |
| 4,335,720 A | 6/1982 | Glassman |
| 4,543,098 A | 9/1985 | Wolfe et al. |
| 4,573,988 A | 3/1986 | Iskra et al. |
| 4,661,101 A | 4/1987 | Sustmann |
| 4,787,699 A | 11/1988 | Moulin |
| 4,787,895 A | 11/1988 | Stokes et al. |
| 4,816,100 A | 3/1989 | Friese |
| 4,859,273 A | 8/1989 | Friese |
| 4,863,450 A | 9/1989 | Friese |
| 4,979,947 A | 12/1990 | Berman |
| 5,185,010 A | 2/1993 | Brown, Jr. |
| 5,300,054 A | 4/1994 | Feist et al. |
| 5,366,450 A | 11/1994 | Degroot |
| 5,439,458 A | 8/1995 | Noel et al. |
| 5,486,167 A | 1/1996 | Dragoo et al. |
| 5,505,719 A | 4/1996 | Cohen et al. |
| 5,525,407 A * | 6/1996 | Yang ........................ 428/218 |
| 5,533,990 A | 7/1996 | Yeo |
| 5,569,226 A | 10/1996 | Cohen et al. |
| 5,592,725 A | 1/1997 | Brinker |
| 5,607,414 A | 3/1997 | Richards et al. |
| 5,681,300 A | 10/1997 | Ahr et al. |
| 5,686,034 A | 11/1997 | Frankham et al. |
| 5,755,906 A | 5/1998 | Achter et al. |
| 5,772,645 A * | 6/1998 | Zadini et al. ................. 604/358 |
| 5,832,576 A | 11/1998 | Leutwyler et al. |
| 5,849,000 A | 12/1998 | Anjur et al. |
| 5,911,712 A * | 6/1999 | Leutwyler et al. ............ 604/379 |
| 6,039,716 A | 3/2000 | Jessup et al. |
| 6,039,828 A | 3/2000 | Achter et al. |
| 6,056,714 A | 5/2000 | McNelis et al. |
| 6,183,457 B1 | 2/2001 | Kuhn |
| 6,186,994 B1 | 2/2001 | Bowles et al. |
| 6,186,995 B1 | 2/2001 | Tharpe, Jr. |
| 6,283,952 B1 | 9/2001 | Child et al. |
| 6,302,862 B1 | 10/2001 | Osborn, III et al. |
| 6,310,269 B1 | 10/2001 | Friese et al. |
| 6,415,484 B1 | 7/2002 | Moser |
| 6,554,814 B1 * | 4/2003 | Agyapong et al. ........ 604/385.18 |
| 6,599,521 B1 | 7/2003 | Resheski Wedepohl et al. |
| 6,682,513 B2 | 1/2004 | Agyapong et al. |
| 6,710,220 B2 | 3/2004 | Kluger et al. |
| 6,889,409 B2 | 5/2005 | Friese et al. |
| 6,899,700 B2 * | 5/2005 | Gehling et al. ............... 604/285 |
| 7,138,559 B2 | 11/2006 | Kluger et al. |
| 8,293,968 B2 * | 10/2012 | Schmidt-Forst et al. ..... 604/365 |
| 2002/0107494 A1 | 8/2002 | Williams |
| 2002/0120246 A1 | 8/2002 | Buzot |
| 2002/0156343 A1 | 10/2002 | Zunker |
| 2003/0023214 A1 | 1/2003 | Disalvo et al. |
| 2003/0176844 A1 | 9/2003 | Randall et al. |
| 2003/0208180 A1 | 11/2003 | Fuchs et al. |
| 2003/0229328 A1 | 12/2003 | Costa |
| 2005/0143708 A1 | 6/2005 | Hagberg et al. |
| 2005/0277904 A1 | 12/2005 | Chase et al. |
| 2005/0283128 A1 | 12/2005 | Chase et al. |
| 2006/0074391 A1 | 4/2006 | Hagberg et al. |
| 2007/0203429 A1 | 8/2007 | Ziv |
| 2007/0260211 A1* | 11/2007 | Schmidt-Forst ......... 604/385.17 |
| 2007/0266503 A1 | 11/2007 | Schmidt-Först et al. |

FOREIGN PATENT DOCUMENTS

| | | | |
|---|---|---|---|
| EP | 0 163 179 A1 | 12/1985 |
| EP | 0 639 363 B1 | 4/1998 |
| EP | 0 965 316 A2 | 12/1999 |
| EP | 1 064 901 A2 | 1/2001 |
| EP | 0 685 213 B1 | 10/2001 |
| EP | 0 716 170 B1 | 2/2002 |
| EP | 0 611 562 B2 | 1/2003 |
| EP | 0 422 660 B2 | 12/2003 |
| EP | 0 735 848 B2 | 12/2003 |
| EP | 1 481 656 A1 | 12/2004 |
| GB | 1 409 172 A | 10/1975 |
| GB | 2 284 992 A | 6/1995 |
| JP | 61-048724 U1 | 4/1986 |
| KR | 10-0899047 B1 | 5/2009 |
| WO | WO 89/07924 A1 | 9/1989 |
| WO | WO 97/23185 A1 | 7/1997 |
| WO | WO 98/47456 * | 10/1998 | ............. A61F 13/15 |
| WO | WO 98/47456 A1 | 10/1998 |
| WO | WO 00/37013 A1 | 6/2000 |
| WO | WO 00/59439 A1 | 10/2000 |
| WO | WO 00/75427 A2 | 12/2000 |
| WO | WO 03/055429 A1 | 7/2003 |
| WO | WO 2004/021943 A1 | 3/2004 |
| WO | WO 2004/113608 A2 | 12/2004 |

* cited by examiner

DUAL MODE ABSORBENT TAMPON

This application claims priority as a continuation application of U.S. application Ser. No. 11/117,899, filed on Apr. 29, 2005. The entirety of application Ser. No. 11/117,899 is incorporated herein by reference,

BACKGROUND

The present invention concerns personal hygiene products, more particularly, catamenial tampons. Currently, there are two basic types of catamenial tampons used for feminine hygiene. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent material into an elongated shape often referred to as a "softwind." The softwind is then radially and/or biaxially compressed into a pledget. The pledget may or may not include a cover. In both types of tampons, a withdrawal string is attached to the absorbent, either before or after compression, to facilitate removal of the tampon from the users vagina after it has absorbed a certain quantity of body fluid, such as menses, blood, etc.

It has been found that many tampons, both digital as well as those delivered by an applicator, are often unable to prevent premature leakage of body fluid. Premature leakage can result from a number of factors. For example, one factor is that the tampon does not properly fit above the introital region of the vagina. Another example is that the tampon is not shaped correctly to intercept fluid flow through the vaginal canal. Still another example is that the folds and convolutions of the vagina are not all in contact with the tampon and therefore body fluid is able to bypass the tampon.

While various types of tampons exist in the art, there remains a need for a tampon product that helps better prevent leakage of body fluid soon after being inserted into a woman's vagina and provides utilization of the absorbent during use. The applicants have surprisingly invented such a tampon, as discussed further herein.

SUMMARY

Various definitions used throughout the specification and claims are provided first, followed by a description of various aspects of the invention.

DEFINITIONS

As used herein forms of the words "comprise", "have", and "include" are legally equivalent and open-ended. Therefore, additional non-recited elements, functions, steps or limitations may be present in addition to the recited elements, functions, steps, or limitations.

As used herein, "disposable" means being disposed of after a single use and not intended to be washed and reused.

As used herein, the term "autogenous bonding", "autogenously bondable" and similar forms of these words, means bonding provided by fusion and/or self-adhesion of fibers and/or filaments without an applied external adhesive or bonding agent. Autogenous bonding can be provided by contact between fibers and/or filaments while at least a portion of the fibers and/or filaments are semi-molten or tacky. Autogenous bonding may also be provided by blending a tackifying resin with the thermoplastic polymers used to form the fibers and/or filaments. Fibers and/or filaments formed from such a blend can be adapted to self-bond with or without the application of pressure and/or heat. Solvents may also be used to cause fusion of fibers and filaments which remain after the solvent is removed.

As used herein, the term "non-cylindrical shape" means a tampon having a second zone of the tampon where the cross-sectional Diameter of the second zone is at least 5% greater than a cross-sectional Diameter of at least a first zone of the tampon, such Diameter of the respective zones being determined according to the Radial Expansion Test herein. Examples not drawn to scale, and rather, slightly exaggerated for illustration purposes, are seen in FIGS. 2, 4 and 6. The at least 5% greater value is believed to readily distinguish the inventive tampons from prior tampons that through manufacturing variability may have had zones with varying Diameters (i.e., none of the prior tampons had first and second zones with Diameters that differed by more than 5%, as well as none of the prior packages of multiple tampons consistently having each tampon in the pack which would have a non-cylindrical shape when the tampon absorbed liquid).

As used herein, the term "cross-section", "cross-sectional" and similar forms of these words, mean the plane which extends laterally through the tampon and which is orthogonal to the longitudinal axis of the tampon.

As used herein, the term "Diameter" and similar forms of this word, means the cross-sectional diameter (22 and 26 are examples) of the tampon as measured according to the Radial Expansion Test herein.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

In response to one or more of the discussed difficulties or problems encountered in the art, a new tampon has been invented that starts out generally cylindrical in shape in a first mode and then becomes non-cylindrical in shape in a second mode to help prevent leakage of body fluid soon after being inserted into a woman's vagina, and which can also, advantageously, provide good utilization of the entire absorbent during use. The purposes and features of the present invention will be set forth in and are apparent from the description that follows, as well as will be learned by practice of the invention. Additional features of the invention will be realized and attained by the product and process particularly pointed out in the written description and claims hereof, as well as from the appended drawings.

In one aspect, the invention provides a dual mode absorbent tampon. The tampon includes a mass of absorbent material compressed into a generally cylindrical shape, in a first mode of the tampon. The mass of absorbent material includes a homogeneous mixture of a plurality of fibers which comprise at least a first type of fiber and a second type of fiber, where the first type of fiber is bondable to fibers of the plurality of fibers. At least a portion of the first type of fibers are bonded in a pre-determined pattern to adjacent fibers of the plurality of fibers wherein absorption of liquid by the tampon causes at least a portion of the mass of absorbent material to expand into a non-cylindrical shape which is dependent upon the pre-determined pattern, in a second mode of the tampon.

In another aspect, the invention provides a dual mode absorbent tampon. The tampon includes a mass of absorbent material compressed into a generally cylindrical shaped, in a first mode of the tampon. The mass of absorbent material includes a plurality of fibers which include a first type of fiber and a second type of fiber, the second type of fiber having a material composition different than the first type of fiber. At least a portion of the first type of fibers are bonded in a pre-determined pattern to adjacent fibers of the plurality of fibers wherein absorption of liquid by the tampon causes at least a portion of the mass of absorbent material to expand into a non-cylindrical shape which is dependent upon the pre-determined pattern, in a second mode of the tampon.

In yet other aspects, the invention provides various configurations and optional features for, the plurality of fibers, the shape of the tampon, and Radial Expansion, and such features, in various combinations, not available in existing tampons.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the disposable absorbent tampons of the invention.

BRIEF DESCRIPTION OF THE DRAWINGS

The drawings are merely representative and are not intended to limit the scope of the claims. Like parts depicted in the drawings are referred to by the same reference numerals.

DETAILED DESCRIPTION

Figure 1:
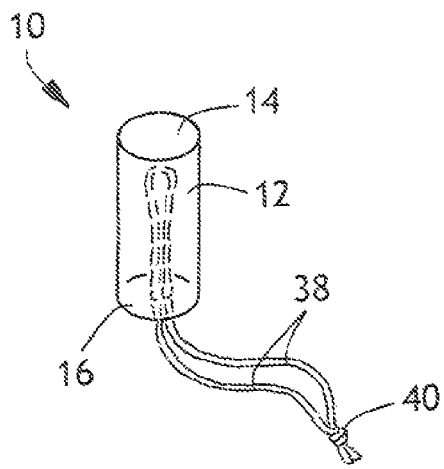
FIG. 1 is a dual mode absorbent tampon of the invention, in the first mode of the tampon.
Figure 3:
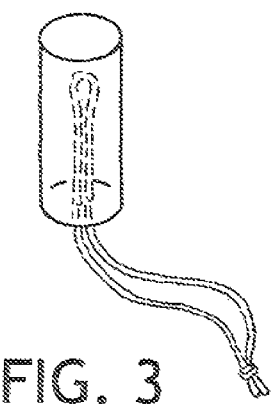
FIG. 3 is an alternate dual mode absorbent tampon of the invention, in the first mode of the tampon.
Figure 5:
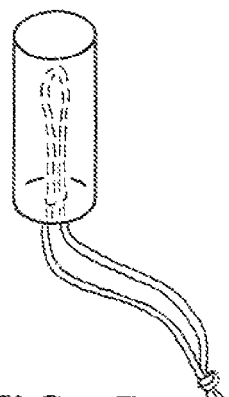
FIG. 5 is another alternate dual mode absorbent tampon of the invention, in the first mode of the tampon.

Referring to the Figures, a variety of forms of dual mode tampon 10 are shown which can be useful for absorbing body fluid from a woman's vagina, especially during her menstrual cycle. The tampon 10 is designed to be inserted above the introital region of a woman's vagina and is designed to function so as to intercept the fluid flow of menses, blood, and other body fluids and prevent the fluid from exiting the vagina. The tampon 10 includes a mass of absorbent material 12 compressed into a generally cylindrical shape, in a first mode of the tampon (e.g., FIGS. 1, 3 and 5). The generally cylindrical shape may have a variety of cross-sectional shapes spanning from a circular cross-section configuration to more of an oval cross-section configuration to more of a square cross-sectional configuration to more of a rectangular cross-sectional configuration. Tampon 10 generally has an insertion end 14 and a trailing end 16. The insertion end 14 is designed to be the first part of the tampon which enters the woman's vaginal cavity. It should be noted that, while in use, the tampon 10 will be entirely positioned within the woman's vagina.

The mass of absorbent material can be formed from absorbent fibers which are assembled into an absorbent sheet or ribbon. One exemplary type of sheet for practicing the invention is described in patent application PCT/EP2004/006441 titled: "Airlaid Process With Improved Throughput", filed Jun. 16, 2003, published Dec. 29, 2004 as WO2004/113608, which is owned by the same assignee as this application and is incorporated herein by reference. Alternatively, the material 12 can be formed from a general mass of absorbent fibers. In either case, the fibers are then rolled or assembled, respectively, and compressed into a generally cylindrical and elongated shape. Two processes for forming such an absorbent sheet are known as "carding" and "airlaying." Depending upon the desired absorbency one desires in the finished tampon, the basis weight of the absorbent sheet can vary. The U.S. Food and Drug Administration (FDA) has set absorbency standards for "junior", "regular", "super", "super-plus" and "super-plus-plus" size tampons. In order to meet the certain standards for these sizes, the absorbent sheets are targeted to have basis weights of about 100 grams per square meter (gsm), 120-150 gsm, 170-180 gsm, 210-230 gsm, and 240-260 gsm, respectively, and as much as 270-290 gsm. Typically, the formation process is controlled to produce an absorbent sheet with a width of between about 40 mm to about 60 mm, preferably about 50 mm. The basis weight and/or the length of the tampon 10 can also be adjusted to form the different size tampons.

Material 12 is a plurality of fibers which include at least a first type of fiber and a second type of fiber. The first type of fiber (also referred to generally herein as binder fiber) is bondable to fibers of the plurality of fibers. Additionally, the plurality of fibers may be a homogeneous mixture of the types of fibers and additionally, or alternatively, the second type of fiber may have a material composition different than the first type of fiber. For example, the bondable first type of fibers may be polymer fibers. Material 12 includes a second type of fiber which may be cellulosic fibers such as wood pulp, cotton, rayon, viscose, LYOCELL® which is from Lenzing Company of Austria, or mixtures of these or other cellulosic fibers. The second type fiber may be a natural type fiber and/or it may not be autogenously bondable to other like type fibers. The absorbent material can be a blend of viscose and binder fibers. Some blends which are believed to work well include a blend of about 70% viscose to about 95% viscose with the remainder about 30% binder fiber to about 5% binder fiber; and more advantageously about 85-90% viscose and the remainder about 15-10% binder fiber. The particular blend of fibers can vary depending upon one's preference in combination with also achieving the features of the invention.

More specifically, for example, the plurality of fibers could be either synthetic fibers or natural fibers, as long as they have the desired absorbent and/or bondable characteristics. Synthetic fibers include those made from polyolefins, polyamides, polyesters, rayon, acrylics, viscose, superabsorbents, LYOCELL® regenerated cellulose and any other suitable synthetic fibers known to those skilled in the art. Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Another fiber could be a bi-component polyester sheath and polyethylene core and known as T255 made by Trevira of Germany. Other polyolefins are also available. Suitable rayon fibers are 1.5 denier Merge 18453 fibers from Acordis Cellulose Fibers Incorporated of Axis, Ala. The fibers can be treated by conventional compositions and/or processes to enable or enhance wettability.

Natural fibers can include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Crimping may be imparted to the fibers, e.g., by conventional means. Curl may be imparted to the fibers, e.g., by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation.

For the cellulosic fiber (e.g., viscose, rayon, etc.), the fibers should have a staple length of between about 5 mm to about 35 mm. The fibers should have a denier of between about 2 to about 6. Denier is a unit of fineness of yarn based on a standard of 50 milligrams (mg) for 450 meters of yarn. The fibers can have a circular, a bi-lobal, a tri-lobal cross-sectional configuration, or some other cross-sectional configuration known to those skilled in the art. The bi-lobal configuration has a cross-sectional profile which looks like a dog bone while the tri-lobal configuration has a cross-sectional profile which looks like a "Y". The fibers can also be bleached if desired.

When cotton fibers are used, the cotton fibers should have a staple length of between about 5 millimeters (mm) to about 20 mm. The cotton fibers should generally have a fiber size of between about 150 microns to about 280 microns. The cotton fibers can also be bleached if desired. Bleaching will make the cotton fibers whiter in appearance.

Figure 2:
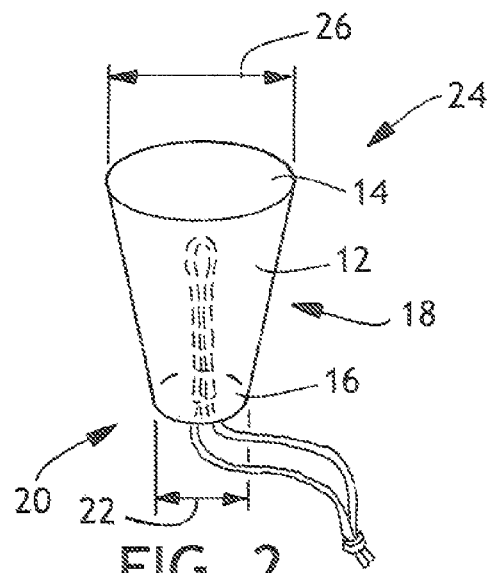
FIG. 2 is the tampon of FIG. 1, in the second mode of the tampon.
Figure 4:
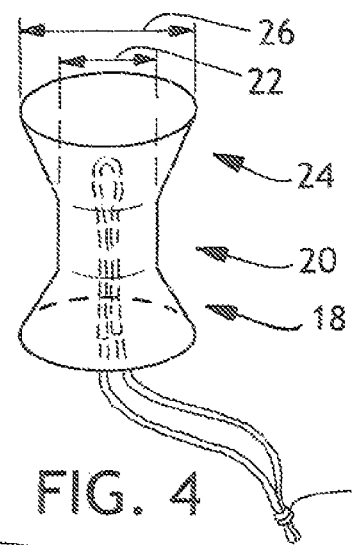
FIG. 4 is the tampon of FIG. 3, in the second mode of the tampon.
Figure 6:
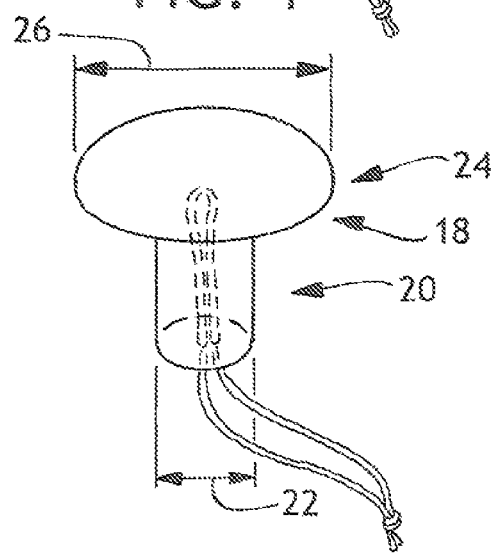
FIG. 6 is the tampon of FIG. 5, in the second mode of the tampon.

The plurality of at least two types of fibers includes a sufficient quantity of the first type of bondable fibers so that when at least a portion of the first type of fibers are bonded in a pre-determined pattern to adjacent fibers of the plurality of fibers, then absorption of liquid by the tampon causes at least a portion of the mass of absorbent material to expand into a non-cylindrical shape 18 which is dependent upon the pre-determined pattern, in a second mode of the tampon (e.g., FIGS. 2, 4 and 6). Although it should be clear, it is by this selective expansion capability that the tampon can provide better and/or more uniform, leakage protection across a broader range of the female population. Said another way, through the pre-determined pattern a portion of the tampon can expand as needed to better fit and the seal the vaginal canal during use of the tampon. The selective expansion of the portion of the tampon into the non-cylindrical shapes 18 occurs because of normal absorbent material expansion characteristics of the mass of absorbent material, as opposed to use of any resilient member (e.g., see U.S. Pat. Nos. 5,755, 906 and 6,039,716, both of assignee Kimberly-Clark Worldwide, Inc., or the like). Rather, the normal absorbent material expansion characteristics of a portion of the cylindrically shaped mass of absorbent material are retarded by bonding (partially to completely, depending on desired total absorption characteristics for the tampon) the first type of fibers in that portion of the tampon (i.e., consistent with the desired pre-determined pattern) to adjacent fibers of the plurality of fibers.

The pre-determined pattern can be achieved in a variety of ways. For example, an adhesive or bonding agent may be applied to, or incorporated into, the tampon to selectively prevent a portion of the tampon from expanding into the non-cylindrical shape to the same degree that another portion does expand when the tampon absorbs liquid. Such adhesive or bonding agent may be applied with the fibers during formation of the mass of absorbent material and then activated to cause bonding between the types of fibers, e.g., activation by heat, radiation and/or pressure.

Advantageously, and additionally or alternatively, the first type of fibers may be autogenously bondable with the first, second, and any other type of fibers in the mass of absorbent material. The inventors have surprisingly found that autogenous bonding can be particularly advantageous because it also simplifies manufacturing of tampons. Without being limited to a theory of understanding, one unexpected and not before possible advantage comes from being able to use a single forming material (i.e., one that includes at least two types of fibers with at least one type of fiber being autogenously bondable, and which may be homogeneous or not so homogeneous if a sufficient quantity of the autogenously bondable fibers are located near the outer surface of the to be formed tampon), as opposed to using two separate materials to make select portions of the tampon so that in use a different and non-cylindrical shape expansion pattern can be obtained by the different rates of expansion of the two different materials. Another unexpected and not before possible advantage comes from being able to use a single forming material (i.e., as just noted previously), and avoid using a conventional cover material over the tampon, because the tampon of the invention with the a sufficient quantity of the autogenously bondable fibers located near the outer surface of the to be formed tampon can be bonded to act like a cover.

For example, for autogenous bonding, such first type of fiber could be thermally bonded to the other fibers, or bonded by other forms of radiation (e.g., microwave, ultrasonics, etc.). With regard to thermal bonding, one skilled in the art will appreciate that the temperature to which the materials, or at least the bond sites thereof, are heated for heat bonding will depend not only on the temperature of the equipment or other heat sources but on the resident time of the materials on the heated surfaces, the compositions of the materials, the basis weights of the materials, their specific heats and thermal conductivities, and, the desired bond strengths in relationship to the pre-determined pattern to be imparted upon the mass of absorbent material and thus resulting expansion into the non-cylindrical shape when absorbing body fluids. Typically, the bonding can be conducted at a temperature of from about 80° C. to about 130° C. Advantageously, the bonding can be conducted at a temperature of from about 90° C. to about 125° C. More advantageously, the bonding can be conducted at a temperature of from about 110° C. to about 120° C. The typical pressure range, on the tampon, can be from about 200 to about 800 kPa (kiloPascals). The preferred pressure range, on the tampon, can be from about 300 to about 600 kPa. However, for a given combination of materials, and in view of the herein contained disclosure, the processing conditions necessary to achieve satisfactory bonding can be readily determined by one of skill in the art.

The bondable fibers, e.g., polymer fibers, can have some tackiness to enhance bonding and autogenous bonding. For example, the polymer itself can be tacky when formed into fibers or, optionally, a compatible tackifying resin can be added to the extrudable polymer compositions described above to provide tackified fibers and/or fibers that autogenously bond. In regard to the tackifying resins and tackified extrudable polymer compositions, note the resins and compositions as disclosed in U.S. Pat. No. 4,787,699, to Moulin. Any tackifier resin can be used which is compatible with the polymer and can withstand the high processing (e.g., extrusion) temperatures. If the polymer is blended with processing aids such as, for example, polyolefins or extending oils, the tackifier resin should also be compatible with those processing aids. Generally, hydrogenated hydrocarbon resins are available tackifying resins, because of their better temperature stability. REGALREZ™ and ARKON™ series tackifiers are examples of hydrogenated hydrocarbon resins. ZONATAK™ 501 Lite is an example of a terpene hydrocarbon. REGALREZ™ hydrocarbon resins are available from Hercules incorporated. ARKON™ series resins are available from Arakawa Chemical (U.S.A.) Inc. The present invention is not limited to use of these tackifying resins, and other tackifying resins which are compatible with the other components of the composition and can withstand the high processing temperatures, can also be used.

The non-cylindrical shape 18 of the tampon when in the second mode may be mushroom shaped (FIG. 6), bottle shaped (FIG. 4), cone shaped (FIG. 2), or any other desired shape whereby one portion maintains more of the original generally cylindrical shape (even if with an expanded cross-section due to expansion with fluid absorption) and another portion expands into an expanded non-cylindrical shape to better assist in sealing the vaginal cavity and absorbing liquid during use. Because it may not be apparent, the shapes depicted in the drawings are not to scale and only generally represent the varying proportional relationships between portions of the tampon 10. Also, the drawings of the tampons (FIGS. 2, 4 and 6) into their expanded shapes represent maximum possible expansions into the depicted non-cylindrical shapes. It should be understood that the tampon would seek to attain this shape inside the vagina in use but that it would be a "soft" expansion with possible irregularities in the non-cylindrical shape in order to accommodate a woman's unique body geometry for fit and comfort while being an absorbent tampon.

Yet further considerations for the non-cylindrical shapes include the non-cylindrical shape being referred to as a first zone 20 and an adjacent second zone 24 (see FIG. 6). The first zone may have a first Diameter 22 corresponding to the generally cylindrical shape and the second zone may have a second Diameter 26 corresponding to the non-cylindrical shape 18 and the second Diameter may be greater than the first Diameter. Further in this regard, and though not required, the second Diameter may be, in degrees of increasing advantage: at least 10% greater, at least 15% greater, at least 20% greater, at least 25% greater and up to 40% greater, than the first Diameter. In this way, the desired sealing features of the tampon 10 may be better implemented, as desired.

The tampon 10 further includes a withdrawal string 38 for assisting in removing the tampon 10 from the woman's vagina. The withdrawal string 38 is attached to the absorbent material 12, and preferably, to the first and second ends, 14 and 16 respectively. One method of attaching the withdrawal string 38 is to form an aperture or hole through the absorbent sheet or ribbon. The withdrawal string 38 is then threaded through the aperture and looped upon itself so as to cinch it secure to the absorbent 12. The free ends of the withdrawal string 38 are then tied in a knot 40 to assure that the withdrawal string 38 will not separate from the material 12. The knot 40 also serves to prevent fraying of the withdrawal string 38 and to provide a place or point where a woman can grasp the withdrawal string 38 when she is ready to remove the tampon 10 from her vagina. It should be noted that the withdrawal string 38 holds the first and second ends, 14 and 16 respectively, in direct contact with one another and may, but need not, limit the amount they can expand while positioned within the woman's vagina. It should be noted that the withdrawal string 38 can be secured to and/or attached to various areas of the tampon 10 and can pass through the absorbent 12. The withdrawal string 38 can also be attached either before the mass of absorbent material 12 is compressed or after it is formed into the tampon.

The withdrawal string 38 can be constructed from various types of threads or ribbons. A thread or ribbon may be made from 100 percent cotton fibers and/or other materials in whole or part. The string may be bonded to the material 12, with or without tying (e.g., using one or more of the ways as for making the pre-determined pattern in material 12) to material 12 before or as material 12 is being formed into the generally cylindrical shape. In this way, there is no need (or less need) for tying the string to the tampon and better assurance that the string will stay in place and attached to the tampon before, during use and during withdrawal of the tampon till it is ready for disposal. Advantageously (though not required because the bonding characteristics of the first type of fibers in the material 12 can be sufficient), and as with the material 12, the string 38 may include bondable material, e.g., the same type of material compositions as for the material 12 or those with similar bonding characteristics. As such, the string may be a plurality of string fibers including at least a first type of string fiber being bondable to adjacent fibers and where the string is autogenous bonded with the mass of absorbent material.

The withdrawal string 38 should have a length which extends beyond the end of the tampon 10 from between about 2 inches to about 8 inches (about 51 mm to about 203 mm), preferably from about 4 inches to about 6 inches (about 102 mm to 152 mm), and most preferably, about 5 inches (about 127 mm). The withdrawal string 38 can be dyed and/or treated with an anti-wicking agent, such as wax, before being secured to the material 12. The anti-wicking agent will facilitate and prevent body fluids from wicking along the withdrawal string 38 and contacting the inner surface of a woman's undergarment. A dry, clean withdrawal string 38 is preferred by the user, especially when she goes to remove the tampon 10 from her vagina.

Tampon 10 may, advantageously, additionally include autogenous bonds located around the surface of the tampon which help impart a smooth appearance to the tampon after removal from packaging and prior to use of the tampon. In this way, the tampon can avoid use of a cover which is traditionally used to impart smoothness and/or better maintain the shape of the tampon prior to and during use.

Example

The following material, for example, is suitable to provide features for tampons of the invention. An airlaid material was produced on a Danweb® Airlaid line containing 93% trilobal rayon fiber (3.3 dtex, 5 mm length) and 7% binder fiber (PET/PE, 3.0 dtex, 6 mm length), with a density of 0.04 g/cc and a basis weight of 180 gsm. This material was cut into rolls of 50 mm width and converted as tampon ribbon on a conventional Ruggli® tampon machine type CL.2/CL 3 into radially wound tampons with a withdrawal string. The tampon was treated with ultrasonic waves using a Branson 8500® machine and a circular sonotrode, at a pressure of 300 kPa and a dwell time of 0.3 sec, in the center section of the tampon (e.g., to impart a pre-determined pattern like FIGS. 3 and 4).

Test Methods

The testing set forth herein is performed where the tampons to be tested are conditioned 24 hours and tested under TAPPI standard conditions of 23±1° C. and 50±2% RH. The test equipment discussed is exemplary and should be used to conduct the testing, however, alternative equipment that is equivalent in all material respects for the given test can be used also (but in the event of conflict between test results the test results from the exemplary equipment shall control).

Radial Expansion Test

After conditioning 10 sample tampons per above, each is treated as follows. Weigh 1000 mL (replenish as needed to be able to saturate all tampons tested) of commercially available saline solution (sodium chloride), 0.9+/−0.005% (w/w) aqueous isotonic saline and pour into a wide mouth beaker capable of holding at least 1500 mL. Drop the sample into the solution and allow to remain there for at least 60 seconds (and no more than 10 minutes) in order to reach saturation capacity (carefully push sample under the surface of the solution if necessary to help begin absorption). Delicately remove the sample being careful to not compress the sample any more than needed to get it to the diameter measuring equipment per the Diameter Measurement Procedure hereafter (in this regard, it is recommended that the visibly smallest diameter portion of the sample be carefully grasped to remove the sample from the solution and get it to the diameter measuring equipment). After removing the sample, hold above the solution beaker for about 2 minutes to allow unabsorbed solution to drip back into the beaker. After the 2 minutes, proceed immediately to the diameter measuring equipment and determine the diameter of the sample using the Diameter Measurement Procedure. Ten samples are tested in this manner and the diameter of each zone for each sample is added together and the collective total diameter for that zone divided by 10, which thereby determines the Diameter, of the respective first or second zone, of the tampon which is discussed herein and set forth in the claims.

Diameter Measurement Procedure

The diameter of an absorbent tampon of the invention is found using the Compression Tester model KES-FB-2 manufactured by Kato Tech Co., Ltd in Japan. The diameter of a sample is found by a single cycle compression of the sample between two circular stainless steel plungers of a tip area of 2 $mm^2$ with a surface measuring 1 mm by 2 mm, for each. The velocity of compression is 1 mm/sec. When the pressure attains a level of 1.0 grams force/$cm^2$ ($gf/cm^2$) the top plunger retracts at the same velocity of 1 mm/sec. The diameter is taken during the compression of the sample at the pressure of 0.5 $gf/cm^2$ as the plungers first move toward each other. This test is first conducted on the first zone (i.e., the one having a diameter corresponding to the generally cylindrical shape) at its visibly narrowest diameter on the sample by placing that spot at the center of the test plunger (i.e., and the plungers having a sufficient spacer attached to their surfaces to avoid compressing the second zone during this part of the measurement), and then operating the test equipment to so measure. After the diameter of the first zone is measured, then the diameter of the second zone (i.e., the one having a diameter corresponding to generally non-cylindrical shape) at its visibly widest diameter on the sample, is measured for that same sample by placing that spot at the center of the test plunger (i.e., and the plungers having the spacer removed so they have a completely smooth surface), and then operating the test equipment to so measure. The diameter of each zone is measured to the closest hundredth of a millimeter for each sample.

All publications, patents, and patent documents cited in the specification are incorporated by reference herein, as though individually incorporated by reference. In the case of any inconsistencies, the present disclosure, including any definitions herein, will prevail. While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

What is claimed is:

1. A dual mode absorbent tampon comprising:
    a mass of absorbent material compressed into a generally cylindrical shape, in a first mode of the tampon;
    the mass of absorbent material comprising a homogeneous mixture of a plurality of fibers which comprise at least a first type of fiber and a second type of fiber, where the first type of fiber is bondable to fibers of the plurality of fibers; and,
    at least a portion of the first type of fibers being bonded in a pre-determined pattern to adjacent fibers of the plurality of fibers wherein absorption of liquid by the plurality of fibers causes at least a portion of the mass of absorbent material to expand into a non-cylindrical shape which is dependent upon the pre-determined pattern, in a second mode of the tampon.

2. The absorbent tampon of claim 1 wherein the second type of fiber is not autogenously bondable to other second type fibers.

3. The absorbent tampon of claim 1 wherein the second type of fiber is a natural type fiber.

4. The absorbent tampon of claim 1 wherein the first type of fiber is autogenously bondable with fibers of the plurality of fibers.

5. The absorbent tampon of claim 1 wherein the first type of fiber is thermally or radiation bonded to adjacent fibers of the plurality of fibers.

6. The absorbent tampon of claim 1 wherein the non-cylindrical shape comprises a member from the group consisting of mushroom shaped, bottle shaped, and cone shaped.

7. The absorbent tampon of claim 1 wherein the non-cylindrical shape comprises a first zone and an adjacent second zone, with the first zone having a first Diameter corresponding to the generally cylindrical shape and the second zone having a second Diameter corresponding to the non-cylindrical shape such that the second Diameter is greater than the first Diameter as measured according to the Radial Expansion Test.

8. The absorbent tampon of claim 1 wherein the non-cylindrical shape comprises a first zone and an adjacent second zone, with the first zone having a first Diameter corresponding to the generally cylindrical shape and the second zone having a second Diameter corresponding to the non-cylindrical shape such that the second Diameter is at least 10% greater than the first Diameter as measured according to the Radial Expansion Test.

9. The absorbent tampon of claim 8 wherein the second Diameter is at least 15% greater than the first Diameter.

10. The absorbent tampon of claim 8 wherein the second Diameter is at least 20% greater than the first Diameter.

11. The absorbent tampon of claim 1 wherein the second type of fiber is a natural type of fiber that does not autogenously bond to other second type fibers.

12. The absorbent tampon of claim 1 wherein the mass of absorbent fibers are formed by airlaying the plurality of first and second type fibers.

13. The absorbent tampon of claim 1 wherein autogenous bonds are located around the surface of the tampon and thereby help impart a smooth appearance to the tampon after removal from packaging and prior to use of the tampon.

14. The absorbent tampon of claim 1 wherein the tampon includes a string attached therewith and the string is bonded with the mass of absorbent material.

15. The absorbent tampon of claim 1 wherein the tampon includes a string attached therewith and the string is autogenous bonded with the mass of absorbent material.

16. The absorbent tampon of claim 1 wherein the tampon includes a string attached therewith and the string comprises a plurality of string fibers including at least a first type of string fiber being bondable to adjacent fibers and the string is autogenous bonded with the mass of absorbent material.

\* \* \* \* \*